(12) United States Patent
Ong

(10) Patent No.: US 7,579,389 B2
(45) Date of Patent: Aug. 25, 2009

(54) ANTIMICROBIAL ACRYLIC POLYMER

(75) Inventor: Ivan Wei-Kang Ong, Charlotte, NC (US)

(73) Assignee: Microban Products Company, Huntersville, NC (US)

( * ) Notice: Subject to any disclaimer, the term of this patent is extended or adjusted under 35 U.S.C. 154(b) by 279 days.

(21) Appl. No.: 10/569,918

(22) PCT Filed: Aug. 26, 2004

(86) PCT No.: PCT/US2004/027756

§ 371 (c)(1),
(2), (4) Date: Feb. 28, 2006

(87) PCT Pub. No.: WO2005/021626

PCT Pub. Date: Mar. 10, 2005

(65) Prior Publication Data

US 2007/0021528 A1    Jan. 25, 2007

Related U.S. Application Data

(60) Provisional application No. 60/498,491, filed on Aug. 28, 2003, provisional application No. 60/536,875, filed on Jan. 16, 2004.

(51) Int. Cl.
| | | |
|---|---|---|
| *C08L 31/00* | (2006.01) | |
| *C09D 5/16* | (2006.01) | |
| *A01N 25/10* | (2006.01) | |
| *A01N 43/04* | (2006.01) | |
| *A61K 31/54* | (2006.01) | |

(52) U.S. Cl. .............. 523/122; 524/556; 424/405; 424/409; 514/23; 514/42; 514/222.2; 514/224.2; 514/226.5; 514/230.8; 514/359; 514/372; 514/383; 514/385

(58) Field of Classification Search ............... 523/122; 524/556; 424/405, 409; 514/23, 42, 222.2, 514/224.2, 226.5, 230.8, 359, 372, 383, 385
See application file for complete search history.

(56) References Cited

U.S. PATENT DOCUMENTS

| | | | |
|---|---|---|---|
| 5,712,275 A | | 1/1998 | Van Gestel |
| 6,149,927 A | * | 11/2000 | Ghosh ..................... 424/405 |
| 2003/0064189 A1 | | 4/2003 | Berg et al. |

FOREIGN PATENT DOCUMENTS

| | | | |
|---|---|---|---|
| WO | WO 95/05739 A1 | | 3/1995 |
| WO | WO 99/47595 | * | 9/1999 |

* cited by examiner

*Primary Examiner*—Kriellion A Sanders
(74) *Attorney, Agent, or Firm*—Cliff D. Weston

(57) ABSTRACT

An antimicrobial additive composition is provided which economically and efficiently imparts antimicrobial characteristics to acrylic polymers, and particularly thermoformable acrylic sheets made from such polymers. The antimicrobial composition comprises an alkyl dimethyl ammonium saccharinate, an oxathiazine, an azole, an isothiazoline, a chlorothalonil, and/or mixtures thereof, among others.

8 Claims, 17 Drawing Sheets

ANTIMICROBIAL ACRYLIC POLYMER

CROSS-REFERENCE TO RELATED APPLICATIONS

The present application claims priority from U.S. provisional application No. 60/498,491 filed on Aug. 28, 2003, and from U.S. provisional application No. 60/536,875 filed on Jan. 16, 2004, each of which is incorporated herein by reference.

BACKGROUND OF THE INVENTION

The present invention relates generally to polymer materials, in particular to polymers which are resistant to the growth of certain microbiological species such as bacteria and fungi. In particular, the present invention relates to sheets of acrylic polymers that are thermoformable.

The acrylics group of polymers is dominated by two resins—one used principally for blending with other resins and as a fiber (polyacrylonitrile or PAN) and the other used principally for molding (polymethylmethacrylate or PMMA). The present invention is directed primarily toward PMMA.

The molding resin, PMMA, is a very popular engineering thermoplastic material. Common brand names for PMMA include Perspex®, Plexiglas®, Lucite®, Acrylite®, Moden-Glass®, and Diakon®. The resin is polymerized by the addition polymerization method and forms a plastic that is atactic and therefore amorphous.

The most important property of PMMA is its optical clarity. This plastic has a very high light transmittance. It is also quite insensitive to UV light. It has low oxidation sensitivity, a high gloss, and overall weather resistance. Together, these characteristics result in a high retention of clarity and light transmittance over long periods of time. These desirable optical properties led to numerous and diverse applications such as windshields (especially for aircraft), skylights, outdoor signs, boat surfaces, automobile tail lights, display cases, light fixtures, shower stalls, spas, bathroom basins, and counter tops, hot tubs, shelving and decorative laminates, among others.

The relatively low processing temperature, low shrinkage, and good dimensional stability make PMMA easy to process in injection molding and extrusion. A major product for PMMA is acrylic sheet which can be thermoformed into many of the products mentioned earlier.

The popularity of acrylic sheets in these applications also means that acrylic sheets are often exposed to high levels of moisture. In the areas of baths, showers, and spas the acrylic material is almost constantly in contact with water. This is especially the case with spas and hot tubs which have considerable fluid volume and are therefore not drained on a regular basis.

Water left in bath basins or spas for only a couple of days can become fouled with numerous biological organisms. In many instances a yellow or brownish scum line develops on the surface of the basin or spa near or at the interface of the standing water and air. With additional aging the water becomes cloudy as algae, bacteria and fungi grow.

Even in areas where water does not stand for extended periods of time, e.g., bathroom sinks and basins, the frequency of wetting can lead to substantial bacterial and fungal growth.

In short, thermoformable acrylic sheeting is often used in applications having high moisture exposure. Thus acrylic sheeting can serve as a growth surface for bacteria, fungi and other microbes that are aesthetically unpleasing, damaging to the product (e.g., cause staining or discoloration), and/or harmful to human health. Accordingly, there is a great need for a control strategy for successfully reducing or substantially eliminating the proliferation of microbes on acrylic surfaces.

The majority of existing control strategies for reducing microbes on acrylic surfaces utilizes treatment of the water by application of chemicals or topical application of antimicrobial agents. For example, in swimming pools and large hot tubs, the algae and the bacteria are usually controlled by the addition of an oxidant such as sodium hypochlorite or an in situ generation of ozone, and by filtering the water through diatomaceous earth. Such treatments are expensive and in small applications, such as a bathroom basin, they are not an option. Bathroom basins and smaller hot tubs and spas typically require the application of topical antimicrobial solutions (e.g., bleach) followed by physical abrasion to remove built up bio-scum. Such topical treatments are time consuming and are not durable.

What is desired is a thermoformable acrylic sheet that has built-in antimicrobial protection that reduces or substantially eliminates the proliferation of bacteria, algae, fungi, and other microbes on its surface. Such an acrylic sheet would also reduce and/or substantially eliminate the need for exterior treatment of the sheet or water.

Attempts at producing such sheeting are known from the prior art. For example, international publication WO 99/47595 discusses a biocidal plastic material comprising an acrylic polymer containing 5% to 50% of a rubbery co-polymer and a biocidal compound. The polymer is purportedly suitable for use in preparing extruded sheets for thermoforming applications. Several biocides are discussed including triclosan, silver, isothiazolones, zinc pyrithione, 10-10' oxybisphenoxyarsine (OBPA), and benzisothiazolin-3-one derivatives.

Similarly, European Patent Application EP 893,473 discusses a thermoplastic acrylic sheet composition that can contain an antimicrobial composition. Trade names for OBPA and isothiazolones are mentioned as possible antimicrobial agents. The '473 document, however, provides no guidance regarding effective amounts of antimicrobial agents or how to incorporate them into the acrylic polymer.

Although some of the known acrylic sheets having built-in antimicrobial agents demonstrate some efficacy against the buildup of microorganisms, there is a continuing need for more efficacious antimicrobial sheeting. The reason for this continuing need is three-fold.

One reason is based in economics. The addition of some antimicrobial products into acrylic polymers increases the per-unit cost of sheeting to levels that are unacceptable to the consumer. The use of silver as an antimicrobial agent is a notable example.

Another reason is based in manufacturing problems. Most industrial acrylic sheet manufacturing processes are precisely controlled processes that produce product with specific characteristics (e.g., optical clarity). The addition of antimicrobial agents often alters the process (e.g., curing time) and/or results in unacceptable product (e.g., opaque sheeting). Inorganic antimicrobial agents such as silver and copper are notable examples in that they tend to discolor thermoformed articles.

Finally, fungal growth remains a problem in spa and bath applications.

Accordingly, there is a need for a commercially acceptable solution to the above discussed problems. This solution should provide an economical alternative to existing antimicrobial acrylic products. This solution should also integrate into existing acrylic sheet manufacturing processes without causing unacceptable process changes. Finally, the solution should demonstrate acceptable efficacy against fungal growth.

BRIEF SUMMARY OF THE INVENTION

The present invention derives from research directed at developing a commercially viable process for making a thermoformable acrylic sheet that exhibits antimicrobial characteristics. One result of this research is an antimicrobial additive composition that exhibits exceptional efficacy against both bacteria and fungus when incorporated into acrylic polymers. In one preferred embodiment, the additive composition according to the invention comprises a quantity of an antimicrobial agent, namely alkyl dimethyl ammonium saccharinates; isothiazolines; oxathiazines; azoles; chlorothalonils; and mixtures thereof.

In a further embodiment the invention encompasses a polymer composition having antimicrobial activity wherein the composition comprises an acrylic polymer and one or more of the above mentioned antimicrobial agents.

In yet another embodiment, the invention encompasses a method of making an antimicrobial polymer composition. In this embodiment and quantity of antimicrobial agent is added to an acrylic polymer material to form an antimicrobial acrylic polymer composition which may then be formed into sheets and other products. The antimicrobial agents used in this embodiment are the same as those used in the other embodiments.

DETAILED DESCRIPTION

Figure 1:
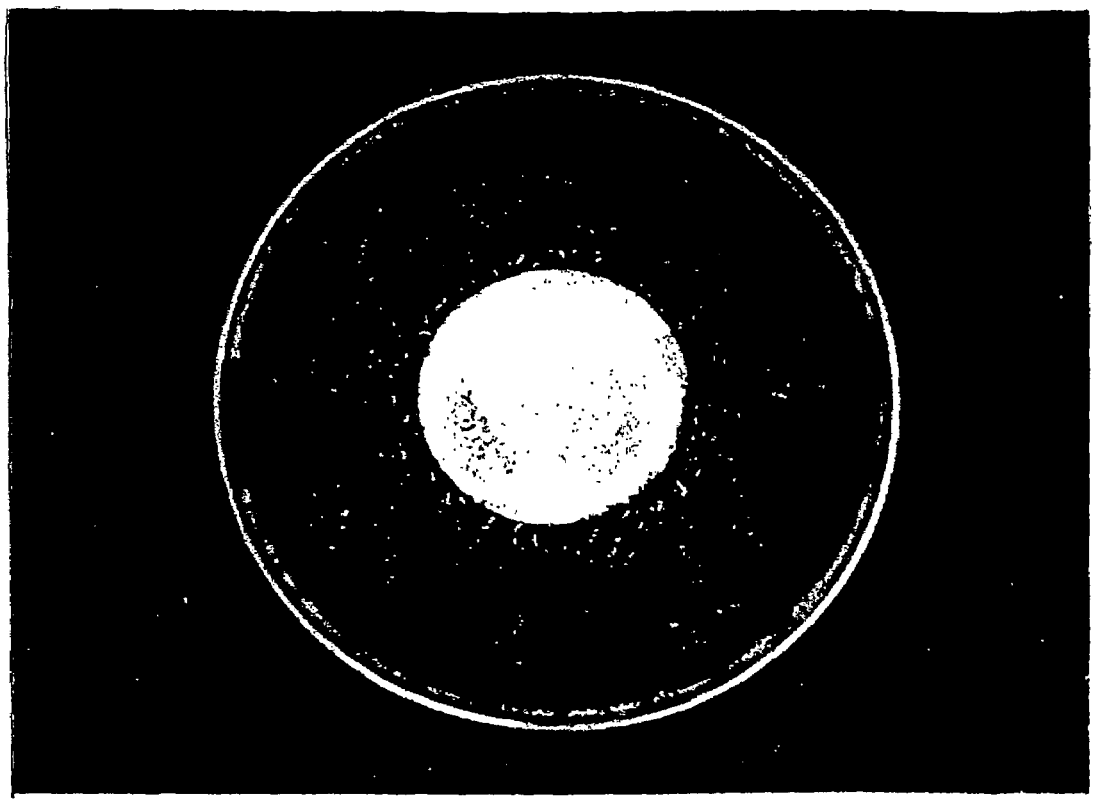
FIG. 1 is a picture of an acrylic disk after plating and incubation.

As used herein, the term "antimicrobial" includes biostatic activity, i.e., where the proliferation of microbiological species is reduced or eliminated, and true biocidal activity where microbiological species are killed. Furthermore, the terms "microbe" or "antimicrobial" should be interpreted to specifically encompass bacteria and fungi as well as other single-celled organisms such as mold, mildew and algae.

As noted previously, the concept of making thermoformable acrylic sheeting having built-in antimicrobial agents is known as evidenced by WO 99/47595 and EP 893,473. Yet, to date, the known thermoformable sheets have not met with a high degree of commercial success for reasons stated previously.

This commercial need led to the present invention, which is, in one broad embodiment, a new combination of acrylic polymers and antifungal agents. The antimicrobial agents utilized in the practice of the invention form an antimicrobial additive composition for imparting antimicrobial characteristics to acrylic polymers, thermoformable acrylic sheets, and articles made from such sheets. In particular, these agents impart antibacterial and antifungal characteristics to thermoformable acrylic sheets at an acceptable cost and without disrupting manufacturing processes and without unacceptably altering the end product.

The antimicrobial additive composition for imparting antimicrobial characteristics to thermoformable acrylic sheets according to the invention comprises a quantity of an antimicrobial agent, namely alkyl dimethyl ammonium saccharinates; isothiazolines; oxathiazines; azoles; chlorothalonils; and mixtures thereof. These agents are commercially available from a number of sources.

Particularly preferred isothiazolines include, but are not limited to, 2-n-octyl-4-isothiazolin-3-one (CAS 26530-20-1) and N-butyl-1,2 benzisothiazolin-3-one (CAS 004299-07-4). 2-n-octyl-4-isothiazolin-3-one is commercially available from Rohm & Hass under the trade name SKANE M-8. N-butyl-1,2 benzisothiazolin-3-one is commonly known as Butyl-BIT (BBIT) and is commercially available from Avecia Chemical under the tradename VANQUISH 100.

A particularly preferred alkyl dimethyl ammonium saccharinate is available under the tradename ONYXIDE 3300 from Stepan Chemicals. ONYXIDE 3300 is described in registration materials as being an alkyl (50% C14, 40% C12, 10% C16) dimethylbenzyl ammonium saccharinate.

Chlorothalonil or 2,4,5,6-Tetrachloroisophthalonitrile (CAS No: 1897-45-6) is commonly known as and sold commercially under the trade name BUSAN 1192 from Buckman Laboratories.

As used herein the term "azoles" should be interpreted to include any of the "azole" antimicrobial agents known to those skilled the art. Particularly preferred azoles include, but are not limited to, propiconazole and tebuconazole and mixtures of these two agents. Mixtures of these two agents have been shown to have a synergistic effect that translates to improved efficacy at lower concentrations of agents.

A particularly preferred oxathiazine is bethoxazin commercially available under the tradename BETHOGARD from Janssen Pharmaceutica.

For ease of discussion the above chemicals are collectively referred to herein as the "antimicrobial agents."

One of the reasons that these antimicrobial agents are used in the practice of the present invention is that they have shown acceptable efficacy at commercially acceptable concentrations. Furthermore, they are soluble in PMMA and PMMA precursors and thus may be seamlessly integrated into existing processes or provided in the form of a premixed masterbatch (i.e., they can be delivered via a polymeric carrier).

In a further embodiment the invention encompasses an acrylic polymer composition having antimicrobial activity. The composition according to the invention comprises an acrylic polymer material and one or more of the above mentioned antimicrobial agents.

The acrylic polymer composition comprises a homopolymer or copolymer of at least one $C_{1-6}$ alkyl ($C_{0-8}$ alk)acrylate. Preferred acrylic materials are homopolymers or copolymers of the methyl, ethyl, butyl, 2-ethylhexyl, cyclohexyl or phenyl esters of acrylic acid or methacrylic acid.

The polymer chemistry underlying the base acrylic material utilized in the practice of the invention is well known among those skilled in the art and will not be discussed in detail herein. As an aid to the reader, however, a brief synopsis of the two primary methods for forming acrylic sheet is provided.

In very general terms, the majority of acrylic sheeting is manufactured in either a casting or an extrusion process. In a very basic extrusion process a quantity of PMMA pellets passed through a heated screwmelter where they are softened and then forced through a slot die into a sheet form. Usually the PMMA pellets are of a homopolymer or a copolymer that is primarily PMMA but this percentage may vary depending upon the particular process, designated end use, or the presence of other additives.

Extrusion processes typically run at fairly high temperatures, e.g., around 200° C., and thus can vaporize or "boil off" organic antimicrobial agents such as those used in the practice of the invention. For example, one popular organic antimicrobial agent is triclosan. Triclosan vaporizes at about 205° C. Accordingly, if organic antimicrobial agents are used in an extrusion process upward adjustments in antimicrobial agent loadings or other precautions such as addition at the end of the extruder may be necessary to ensure sufficient retention of antimicrobial agent in the final product.

The other primary sheet making process is a casting process. The casting process begins by making an acrylic "syrup" which in one basic form is a solution of PMMA polymer dissolved in MMA monomer that has been initiated with a peroxide or UV light. Acrylic syrup can also be made by interrupting the polymerization process before the chains get very long.

After the syrup is made it is cast on a long, flat form to create a sheet which is then allowed to cure. After the sheet has cured to the proper degree it can be manipulated and thermoformed in accordance with processes well known to those skilled in the art.

The invention may be utilized using either an extrusion or a casting process and may be utilized in either a continuous or batch process. Casting processes, however, are particularly well suited to the practice of the invention. The invention is also suitable with curing conducted at room temperature or at an elevated temperature, and is thus compatible with many different cure chemistries.

The composition of the acrylic material is selected according to the application in which the material is to be used. For example, if the material is intended to be cast in a sheet for subsequent thermoforming, e.g., to form a tub or spa; then an acrylic material formulated for casting and thermal molding should be selected. Likewise, if the material is intended to be extruded those skilled in the art may alter the composition for extrusion purposes without undue experimentation.

In preferred embodiments the combined weight concentration of the antimicrobial agent in the polymer composition (also known as the "active level") is in a range from about 250 ppm to about 50,000 ppm based upon the weight of the polymer. In particularly preferred embodiments the antimicrobial agent is present in the polymer composition in a concentration range from about 500 ppm to about 10,000 ppm. More particularly preferred embodiments utilize a range from about 2000 ppm to about 6000 ppm.

If a combination of tebuconazole and propiconazole is used the broadest preferred range for the tebuconazole and propiconazole ratio is between about 90:10 and 10:90 tebuconazole to propiconazole. A more preferred range is between about 60:40 and 40:60 tebuconazole to propiconazole. 50:50 ratios are particularly preferred.

The polymeric material of the invention may have many applications. It is useful as a resin for molding or extrusion applications, e.g., to make doors or panels for interior or exterior cladding applications etc. It may be provided in the form of a sheet material, e.g., for providing walls, linings, etc., or which may be suitable for forming into articles such as bathtubs, shower stalls, etc., by thermoforming. It may also be useful in the form of a curable resin, e.g., a polymethyl methacrylate resin dissolved in methyl methacrylate and optionally containing a dispersion of fillers, colors and other functional particles for the manufacture of sinks, worktops, countertops, etc.

A still further use of the polymer composition according to the invention is as a coating over a base material. One benefit of this form of the invention is that a relatively small amount of the antimicrobials active polymer may be used to give antimicrobial function to the surface of a non-antimicrobial structure. The base material may be another polymer, such as another acrylic layer, polyvinylchloride, or a styrene based polymer for example.

The invention also embodies a method for manufacturing an antimicrobial acrylic polymer composition. The method comprises the steps of combining a quantity of antimicrobial agent with an acrylic polymer material to form an antimicrobial acrylic polymer composition wherein the combined weight concentration of the antimicrobial agent in the polymer composition is in a range from about 250 ppm to about 50,000 ppm based upon the weight of the polymer composition. In particularly preferred embodiments the antimicrobial agent is added to the polymer composition to provide a final concentration in a range from about 500 ppm to about 10,000 ppm. More particularly, preferred embodiments utilize a range from about 2000 ppm to about 6000 ppm.

If a combination of tebuconazole and propiconazole is used the preferable ratio of tebuconazole to propiconazole is between about 90:10 and 10:90, more preferably between about 60:40 and about 40:60, and most preferably around 50:50.

The antimicrobial agents can be combined with the acrylic polymer in several ways. For example, the antimicrobial agents may be combined with the polymer post-polymerization in an extruder.

A more preferred method for combining the antimicrobial agent with the acrylic polymer is to mix the antimicrobial agent with one of the precursors of the acrylic polymer. For example, the antimicrobial agents may be added to the MMA prior to combining the MMA with PMMA to make the acrylic syrup. Alternatively, the antimicrobial agents can be added to the syrup before the syrup is cast. This addition can be directly to the syrup prior to a mixing step or by adding via premixed sidestream as a solution in MMA with other ingredients.

In a still further embodiment the invention encompasses a method of manufacturing a thermoformable antimicrobial acrylic sheet. In broad terms the method comprises the steps of combining a quantity of antimicrobial agent with an acrylic polymer material to form an antimicrobial acrylic polymer composition then forming the antimicrobial acrylic composition into a sheet.

The preferred weight concentrations and weight ratios of antimicrobial agents utilized in this embodiment of the invention are the same as those utilized in previous embodiments and need not be repeated here.

In preferred embodiments the step of combining a quantity of antimicrobial agent with an acrylic polymeric material to form an antimicrobial acrylic polymer composition comprises the step of mixing the antimicrobial agent into a polymeric precursor of the acrylic polymeric material. This precursor may be one of the individual components that make up the acrylic such as methyl methacrylate (MMA) or the acrylic polymer syrup that is made in casting applications. The antimicrobial agents can also be added post-polymerization in an extruder.

After the antimicrobial agent is added to the polymer material the method further comprises forming the resulting polymer composition into a thermoformable acrylic sheet. The preferred methods of forming the sheet are casting or extrusion as known by those skilled in the art and discussed above.

After the sheet is formed it may then be thermoformed or otherwise modified using known methods to create any number of products including but not limited to windshields (especially for aircraft), skylights, outdoor signs, boat surfaces, automobile tail lights, display cases, light fixtures, shower stalls, spas, bathroom basins, and counter tops, hot tubs, shelving and decorative laminates.

EXAMPLES

The following examples are provided as an aid to the reader and should not be interpreted as limiting the scope of the invention in any way. Those skilled in the art are well aware that there are numerous modifications that can be made in the manufacture of acrylic polymer (e.g., casting formulations vs. extrusion formulations). The claimed invention is capable of adaptation to these various alternatives without undue experimentation.

Example 1

A 50 gram sample of acrylic syrup of approximately 10% PMMA and 89.5% MMA and 0.5% antimicrobial agent was prepared. The antimicrobial agent was bethoxazin commercially available as BETHOGARD from Janssen Pharmaceutica. The syrup consisted of
    about 43.9 grams of MMA
    about 0.25 grams of BETHOGARD
    about 4.91 grams of PMMA
    about 0.1 grams of CaOH
    about 0.1 grams (0.1 ml) $H_2O$
    about 0.25 grams (0.3 ml) L. mercaptan
    about 0.5 grams ESPEROX 41-25 (Tert-butyl monoperoxymaleate)

This material was then cast into small circular silicone molds and allowed to cure. Curing was conducted at room temperature. After 24 hours translucent acrylic disks were removed from the molds and evaluated for efficacy.

Each disk demonstrated acceptable efficacy at or below approximately 5000 ppm antimicrobial agent based upon the weight of the polymer.

Example 2

Approximately 50 gram samples of each of the following antimicrobial acrylic compositions were prepared to be cast into disks:

(a) Antimicrobial Syrup at 5000 ppm (0.5% Final Level in Formulation) of Butyl-BIT This composition contained approximately 5000 ppm of active antimicrobial agent. The antimicrobial agent used in this composition was Butyl-BIT (i.e., VANQUISH 100) which is approximately 100% active ingredient. The components of the composition are set forth in Table 1.

TABLE 1

| Component | % of Composition | Weight in Grams or Milliliters |
|---|---|---|
| Syrup (approx. 25% PMMA; approx. 75% MMA with inhibitors) | 97.6 | 48.8 g |
| VANQUISH 100 | 0.5 | 0.25 g |
| CaOH | 0.2 | 0.1 g |
| $H_2O$ | 0.2 | 0.1 g (0.1 ml) |
| Lauryl Mercaptan | 0.5 | 0.25 g (0.3 ml) |
| Esperox 41-25 | 1.0 | 0.5 g |

(b) Antimicrobial Syrup at 7500 ppm (0.75% Final Level in Formulation) of Butyl-BIT This composition contained approximately 7500 ppm of active antimicrobial agent. The antimicrobial agent used in this composition was Butyl-BIT (i.e., VANQUISH 100) which is approximately 100% active ingredient.

TABLE 2

| Component | % of Composition | Weight in Grams or Milliliters |
|---|---|---|
| Syrup (approx. 25% PMMA; approx. 75% MMA with inhibitors) | 97.1 | 48.55 |
| VANQUISH 100 | 1.0 | 0.375 |
| CaOH | 0.2 | 0.1 |
| $H_2O$ | 0.2 | 0.1 g (0.1 ml) |
| Lauryl Mercaptan | 0.5 | 0.25 g (0.3 ml) |
| Esperox 41-25 | 1.0 | 0.5 g |

(c) Antimicrobial Syrup at 5000 ppm of 2-n-octyl-4-isothiazolin-3-one

This composition contained approximately 5000 ppm of active antimicrobial agent. The antimicrobial agent used in this composition was 2-n-octyl-4-isothiazolin-3-one (i.e. SKANE-M8) which is approximately 45% active ingredient.

TABLE 3

| Component | % of Composition | Weight in Grams or Milliliters |
| --- | --- | --- |
| Syrup (approx. 25% PMMA; approx. 75% MMA with inhibitors) | 96.99 | 48.495 g |
| SKANE-M8 | 1.11 | 0.555 g |
| CaOH | 0.2 | 0.1 g |
| $H_2O$ | 0.2 | 0.1 g (0.1 ml) |
| Lauryl Mercaptan | 0.5 | 0.25 g (0.3 ml) |
| Esperox 41-25 | 1.0 | 0.5 g |

(d) Antimicrobial Syrup at 7500 ppm of 2-n-octyl-4-isothiazolin-3-one

This composition contained approximately 7500 ppm of active antimicrobial agent. The antimicrobial agent used in this composition was 2-n-octyl-4-isothiazolin-3-one (i.e. SKANE M-8) which is approximately 45% active ingredient.

TABLE 4

| Component | % of Composition | Weight in Grams or Milliliters |
| --- | --- | --- |
| Syrup (approx. 25% PMMA; approx. 75% MMA with inhibitors) | 96.43 | 48.215 |
| SKANE-M8 | 1.67 | 1.11 |
| CaOH | 0.2 | 0.1 g |
| $H_2O$ | 0.2 | 0.1 g (0.1 ml) |
| Lauryl Mercaptan | 0.5 | 0.25 g (0.3 ml) |
| Esperox 41-25 | 1.0 | 0.5 g |

(e) Antimicrobial Syrup at 5000 ppm of Bethoxazin.

This composition contained approximately 5000 ppm of active antimicrobial agent. The antimicrobial agent used in this composition was Bethoxazin (i.e. BETHOGARD) which is approximately 100% active ingredient.

TABLE 5

| Component | % of Composition | Weight in Grams or Milliliters |
| --- | --- | --- |
| Syrup (approx. 25% PMMA; approx. 75% MMA with inhibitors) | 97.6 | 48.8 g |
| BETHOGARD | 0.5 | 0.25 g |
| CaOH | 0.2 | 0.1 g |
| $H_2O$ | 0.2 | 0.1 g (0.1 ml) |
| Lauryl Mercaptan | 0.5 | 0.25 g (0.3 ml) |
| Esperox 41-25 | 1.0 | 0.5 g |

(f) Antimicrobial Syrup at 7500 ppm of Bethoxazin

This composition contained approximately 7500 ppm of active antimicrobial agent. The antimicrobial agent used in this composition was Bethoxazin (i.e. BETHOGARD) which is approximately 100% active ingredient.

TABLE 6

| Component | % of Composition | Weight in Grams or Milliliters |
| --- | --- | --- |
| Syrup (approx. 25% PMMA; approx. 75% MMA with inhibitors) | 97.1 | 48.55 |
| BETHOGARD | 1.0 | 0.375 |
| CaOH | 0.2 | 0.1 g |
| $H_2O$ | 0.2 | 0.1 g (0.1 ml) |
| Lauryl Mercaptan | 0.5 | 0.25 g (0.3 ml) |
| Esperox 41-25 | 1.0 | 0.5 g |

Each of the above acrylic compositions were prepared and cast into disks by the following method. The amount of acrylic syrup was weighed into a disposable plastic beaker. Liquid additives were weighed directly in the beaker. The solution was stirred completely. Calcium hydroxide powder was added by weighing it out onto weigh paper, then pouring into solution, and stirring completely. The solution was stirred using a magnetic stir bar. Water and Lauryl Mercaptan were added next volumetrically using a graduated pipette. The solution was stirred completely. Esperox 41-25 was added directly to the beaker and stirred in completely. A small reaction occurred forming bubbles and causing a slight color change to a very light orange. The solution was poured into silicone molds within two minutes of adding Esperox 41-25 and allowed to cure. Curing was conducted at room temperature. The compositions were each tested in accordance with AATCC Test Method 30 Part III. The test organism was *Aspergillus niger* 6275.

As specified by the test method, the disks were plated in the middle of a nutrient agar lawn seeded with *Aspergillus niger*. In addition, nutrient agar containing the specified concentration of *Aspergillus niger* was poured on the surface of the test samples.

Fresh acrylic surfaces are typically extremely smooth. Therefore, the sample surfaces were crosshatched with a razor blade to roughen the surface and improve inoculum retention. Roughening the surface improves the "bite" and assists the fungal organisms in anchoring and rooting to the surface.

The test samples were then incubated for a period of 7 days in a controlled chamber with high humidity. Exemplary test results are provided in the figures.

FIG. 1 shows an example of a plated acrylic sample after a period of Incubation.

Figure 2:
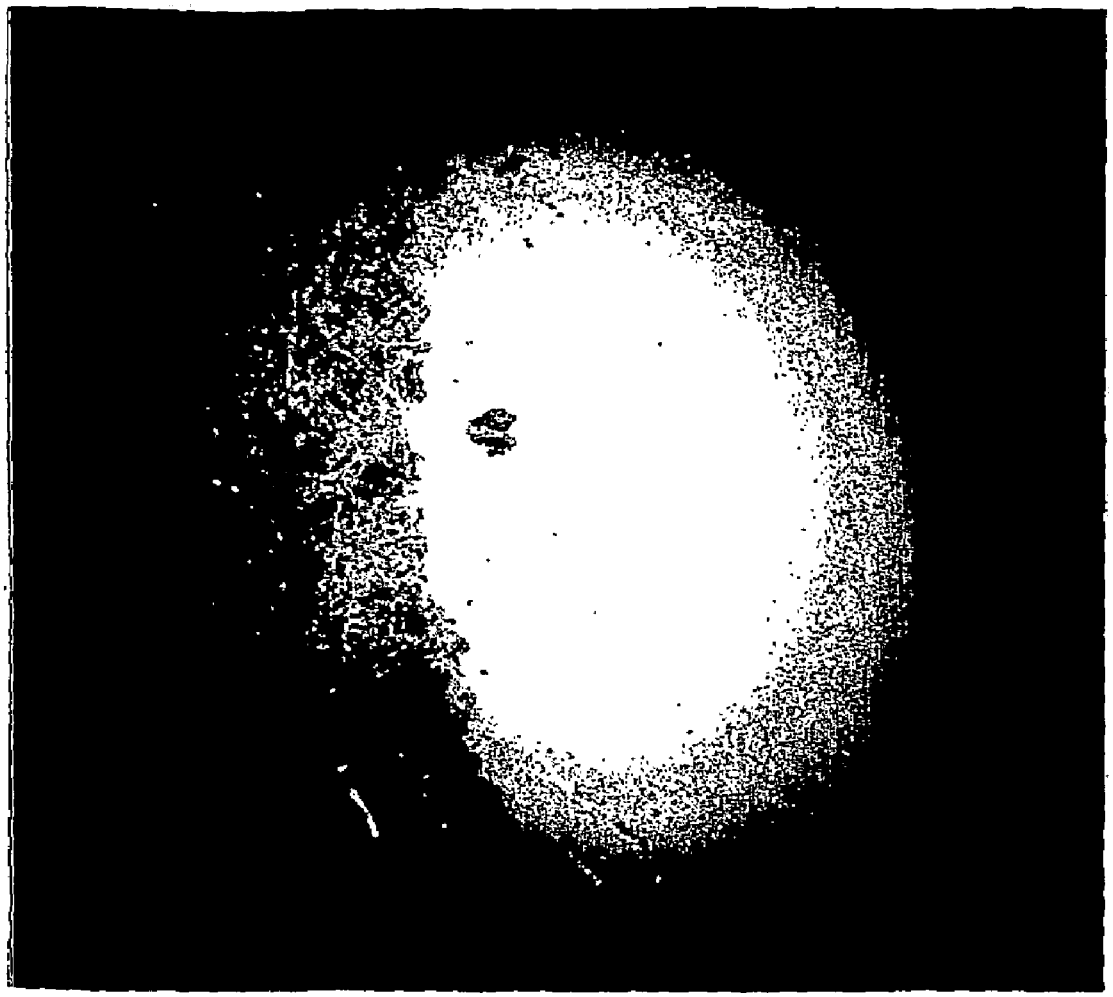
FIG. 2 is a picture of an acrylic disk that contains no antimicrobial agent after inoculation with a fungal species.

FIG. 2 is a picture taken along the edge of a section of a control disk which contained no antimicrobial agent. Significant fungal overlap was present along the edges of the disk. (Note the dark dots within the light colored region.)

Figure 3:
FIG. 3 is a picture taken along the edge of a disk made from the composition described in Table 1 of the Examples after inoculation with a fungal species.

FIG. 3 is a picture taken along the edge of a disk made from the composition described in Table 1. The edges of the disk were free of fungal overlap.

Figure 4:
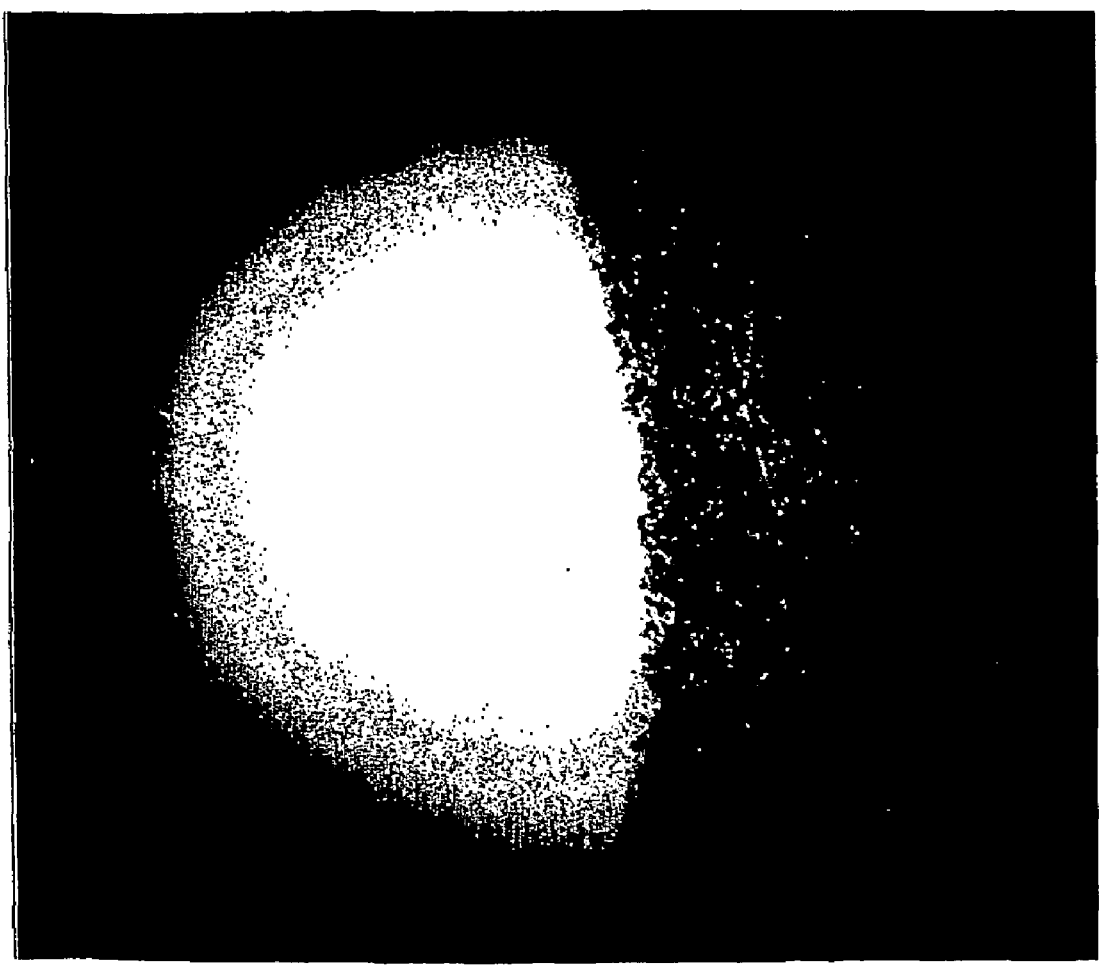
FIG. 4 is a picture taken along the edge of a disk made from the composition described in Table 2 of the Examples after inoculation with a fungal species.

FIG. 4 is a picture taken along the edge of a disk made from the composition described in Table 2. The edges of the disk were free of fungal overlap.

Figure 5:
FIG. 5 is a picture taken along the edge of a disk made from the composition described in Table 3 of the Examples after inoculation with a fungal species.

FIG. 5 is a picture taken along the edge of a disk made from the composition described in Table 3. There was good antifungal efficacy.

Figure 6:
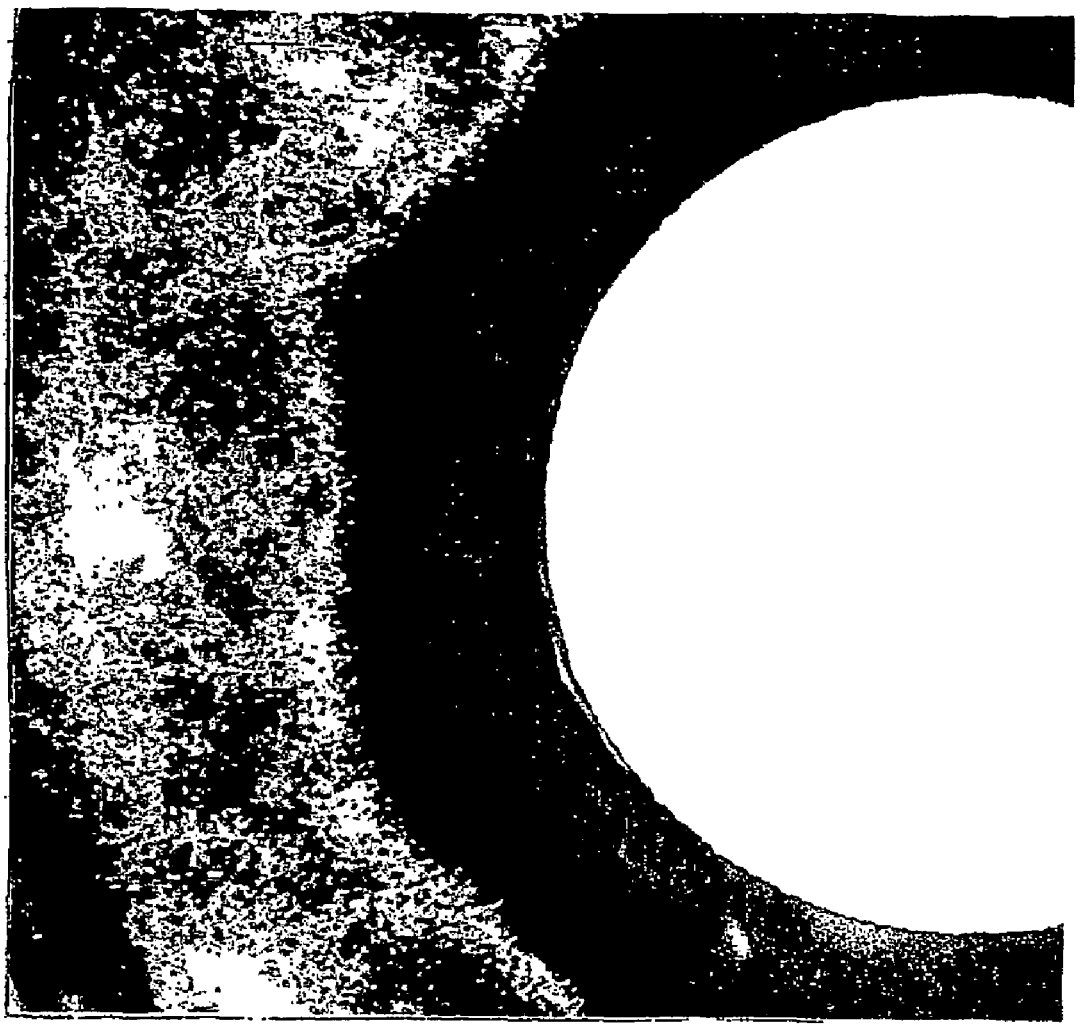
FIG. 6 is a picture taken along the edge of a disk made from the composition described in Table 4 of the Examples after inoculation with a fungal species.

FIG. 6 is a picture taken along the edge of a disk made from the composition described in Table 4. Excellent antifungal efficacy was demonstrated and there was a zone of exclusion of 7 mm to 9 mm around the disk.

Figure 7:
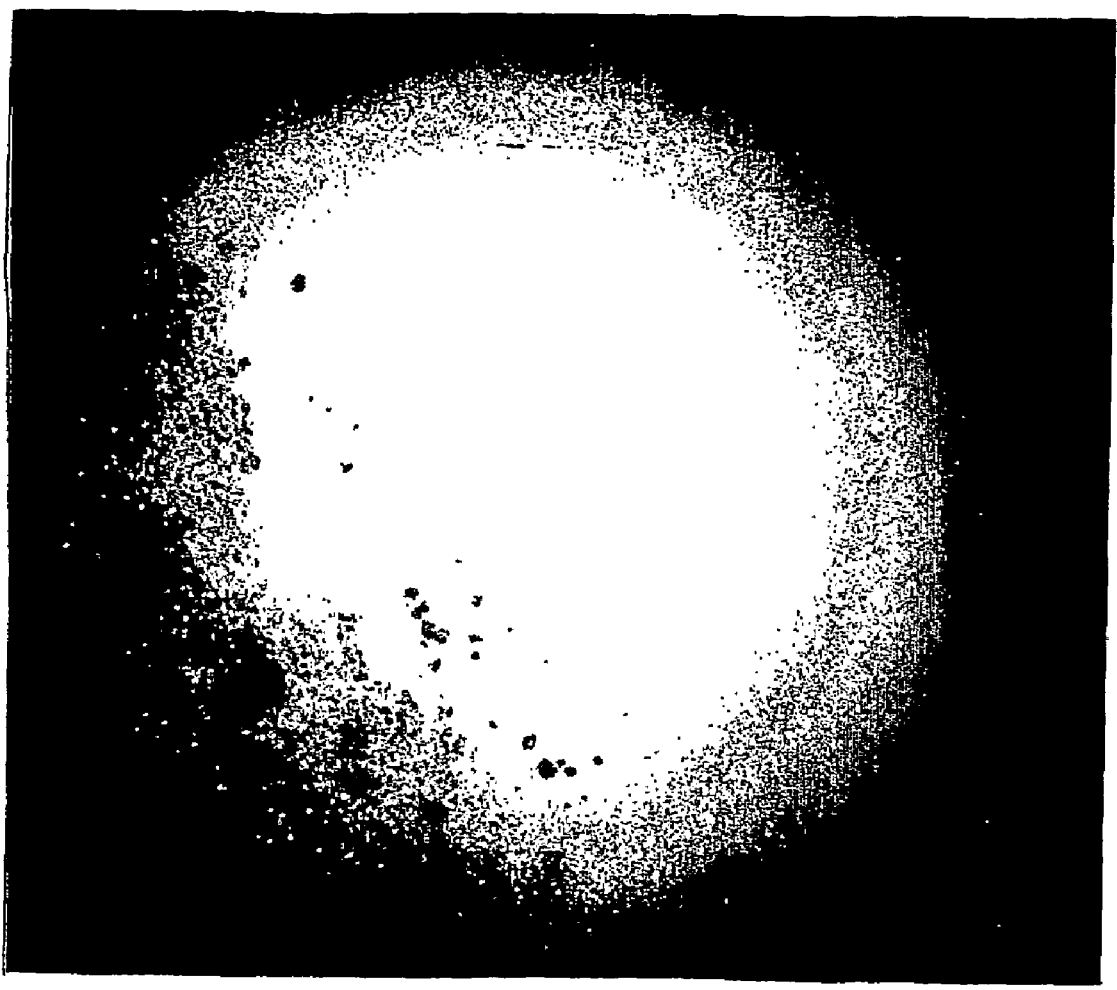
FIG. 7 is a picture taken along the edge of a disk made from the composition described in Table 5 of the Examples after inoculation with a fungal species.

FIG. 7 is a picture taken along the edge of a disk made from the composition described in Table 5. The edges of the disk showed significant fungal overlap.

Figure 8:
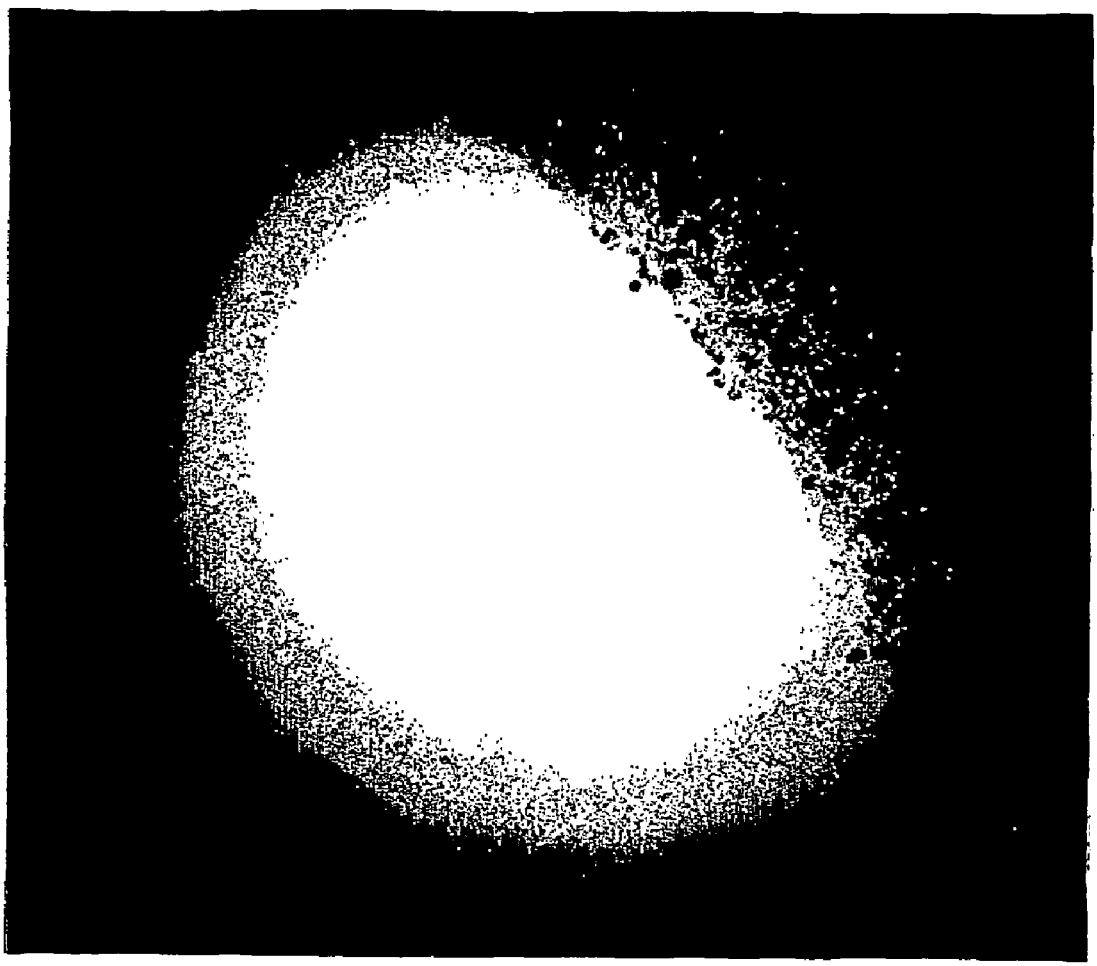
FIG. 8 is a picture taken along the edge of a disk made from the composition described in Table 6 of the Examples after inoculation with a fungal species.

FIG. 8 is a picture taken along the edge of a disk made from the composition described in Table 6. The edge of the disk showed signs of impending fungal overlap.

Example 3

Approximately 50 gram samples of each of the following antimicrobial acrylic compositions were prepared to be cast into disks:

(a) Antimicrobial Syrup at 10,000 ppm (1% Final Level in Formulation) of 2-n-octyl-4-isothiazolin-3-one This composition contained approximately 10,000 ppm of active antimicrobial agent. The antimicrobial agent used in this composition was 2-n-octyl-4-isothiazolin-3-one (i.e. SKANE M-8) which is approximately 45% active ingredient.

TABLE 7

| Component | % of Composition | Weight in Grams or Milliliters |
|---|---|---|
| Syrup (approx. 25% PMMA; approx. 75% MMA with inhibitors) | 95.88 | 47.94 g |
| SKANE M-8 | 2.22 | 1.11 g |
| CaOH | 0.2 | 0.1 g |
| H$_2$O | 0.2 | 0.1 g (0.1 ml) |
| Lauryl Mercaptan | 0.5 | 0.25 g (0.3 ml) |
| Esperox 41-25 | 1.0 | 0.5 g |

(b) Antimicrobial Syrup at 10,000 ppm of Triclosan.

This composition contained approximately 10,000 ppm of active antimicrobial agent. The antimicrobial agent used in this composition was triclosan (i.e. IRGASAN DP 300) which is approximately 100% active ingredient.

TABLE 8

| Component | % of Composition | Weight in Grams or Milliliters |
|---|---|---|
| Syrup (approx. 25% PMMA; approx. 75% MMA with inhibitors) | 97.1 | 48.55 g |
| IRGASAN DP 300 | 1.0 | 0.5 g |
| CaOH | 0.2 | 0.1 g |
| H$_2$O | 0.2 | 0.1 g (0.1 ml) |
| Lauryl Mercaptan | 0.5 | 0.25 g (0.3 ml) |
| Esperox 41-25 | 1.0 | 0.5 g |

(c) Antimicrobial Syrup at 10,000 ppm of Mixture of Propiconazole and Tebuconazole This composition contained approximately 10,000 ppm of a mixture of active antimicrobial agents. The antimicrobial agents used in this composition were in a 1:1 ratio and were propiconazole (i.e. WOCOSEN TECHNICAL) and tebuconazole (i.e. PREVENTOL A8), which are each approximately 100% active ingredient.

TABLE 9

| Syrup (approx. 25% PMMA; approx. 75% MMA with inhibitors) | 97.1 | 48.55 g |
|---|---|---|
| WOCOSEN/PREVENTOL A8 | 1.0 | 0.5 g |
| CaOH | 0.2 | 0.1 g |
| H$_2$O | 0.2 | 0.1 g (0.1 ml) |
| Lauryl Mercaptan | 0.5 | 0.25 g (0.3 ml) |
| Esperox 41-25 | 1.0 | 0.5 g |

(d) Antimicrobial Syrup at 10,000 ppm of Butyl-BIT

This composition contained approximately 10,000 ppm of active antimicrobial agent. The antimicrobial agent used in this composition was Butyl-BIT (i.e. VANQUISH 100) which is approximately 100% active ingredient.

TABLE 10

| Syrup (approx. 25% PMMA; approx. 75% MMA with inhibitors) | 97.1 | 48.55 g |
|---|---|---|
| VANQUISH 100 | 1.0 | 0.5 g |
| CaOH | 0.2 | 0.1 g |
| H$_2$O | 0.2 | 0.1 g (0.1 ml) |
| Lauryl Mercaptan | 0.5 | 0.25 g (0.3 ml) |
| Esperox 41-25 | 1.0 | 0.5 g |

(e) Antimicrobial Syrup at 10,000 ppm of Bethoxazin

This composition contained approximately 10,000 ppm of active antimicrobial agent. The antimicrobial agent used in this composition was Bethoxazin (i.e. BETHOGARD) which is approximately 100% active ingredient.

TABLE 11

| Syrup (approx. 25% PMMA; approx. 75% MMA with inhibitors) | 97.1 | 48.55 g |
|---|---|---|
| BETHOGARD | 1.0 | 0.5 g |
| CaOH | 0.2 | 0.1 g |
| H$_2$O | 0.2 | 0.1 g (0.1 ml) |
| Lauryl Mercaptan | 0.5 | 0.25 g (0.3 ml) |
| Esperox 41-25 | 1.0 | 0.5 g |

(f) Antimicrobial Syrup at 10,000 ppm of Alkyl Dimethylbenzyl Ammonium Saccharinate This composition contained approximately 10,000 ppm of active antimicrobial agent. The antimicrobial used in this composition was alkyl dimethylbenzyl ammonium saccharinate (i.e. ONYXIDE 3300) which is approximately 100% active ingredient.

TABLE 12

| Syrup (approx. 25% PMMA; approx. 75% MMA with inhibitors) | 97.1 | 48.55 g |
|---|---|---|
| ONYXIDE 3300 | 1.0 | 0.5 g |
| CaOH | 0.2 | 0.1 g |
| H$_2$O | 0.2 | 0.1 g (0.1 ml) |
| Lauryl Mercaptan | 0.5 | 0.25 g (0.3 ml) |
| Esperox 41-25 | 1.0 | 0.5 g |

(g) Antimicrobial Syrup at 10,000 ppm of Chlorothalonil

This composition contained approximately 10,000 ppm of active antimicrobial agent. The antimicrobial used in this composition was chlorothalonil (i.e. BUSAN 1192) which is approximately 100% active ingredient.

TABLE 13

| Syrup (approx. 25% PMMA; approx. 75% MMA with inhibitors) | 97.1 | 48.55 g |
|---|---|---|
| BUSAN 1192 | 1.0 | 0.5 g |
| CaOH | 0.2 | 0.1 g |
| H$_2$O | 0.2 | 0.1 g (0.1 ml) |
| Lauryl Mercaptan | 0.5 | 0.25 g (0.3 ml) |
| Esperox 41-25 | 1.0 | 0.5 g |

Each of the above acrylic compositions were prepared and cast into disks by the following method. The amount of acrylic syrup was weighed into a disposable plastic beaker. Liquid additives were weighed directly in the beaker. The solution was stirred completely. Calcium hydroxide powder was added by weighing it out onto weigh paper, then pouring into solution, and stirring completely. The solution was stirred using a magnetic stir bar. Water and Lauryl Mercaptan were added next volumetrically using a graduated pipette. The solution was stirred completely. Esperox 41-25 was added directly to the beaker and stirred in completely. A small reaction occurred forming bubbles and causing a slight color change to a very light orange. The solution was poured into silicone molds within two minutes of adding Esperox 41-25 and allowed to cure. Curing was conducted at room temperature. The compositions were each tested in accordance with AATCC Test Method 30 Part III. The test organism was *Aspergillus niger* 6275.

As specified by the test method, the disks were plated in the middle of a nutrient agar lawn seeded with *Aspergillus niger*.

In addition, nutrient agar containing the specified concentration of *Aspergillus niger* was poured on the surface of the test samples.

Fresh acrylic surfaces are typically extremely smooth. Therefore, the sample surfaces were crosshatched with a razor blade to roughen the surface and improve inoculum retention. Roughening the surface improves the "bite" and assists the fungal organisms in anchoring and rooting to the surface.

The test samples were then incubated for a period of 7 days in a controlled chamber with high humidity. Exemplary test results are provided in the figures.

Figure 9:
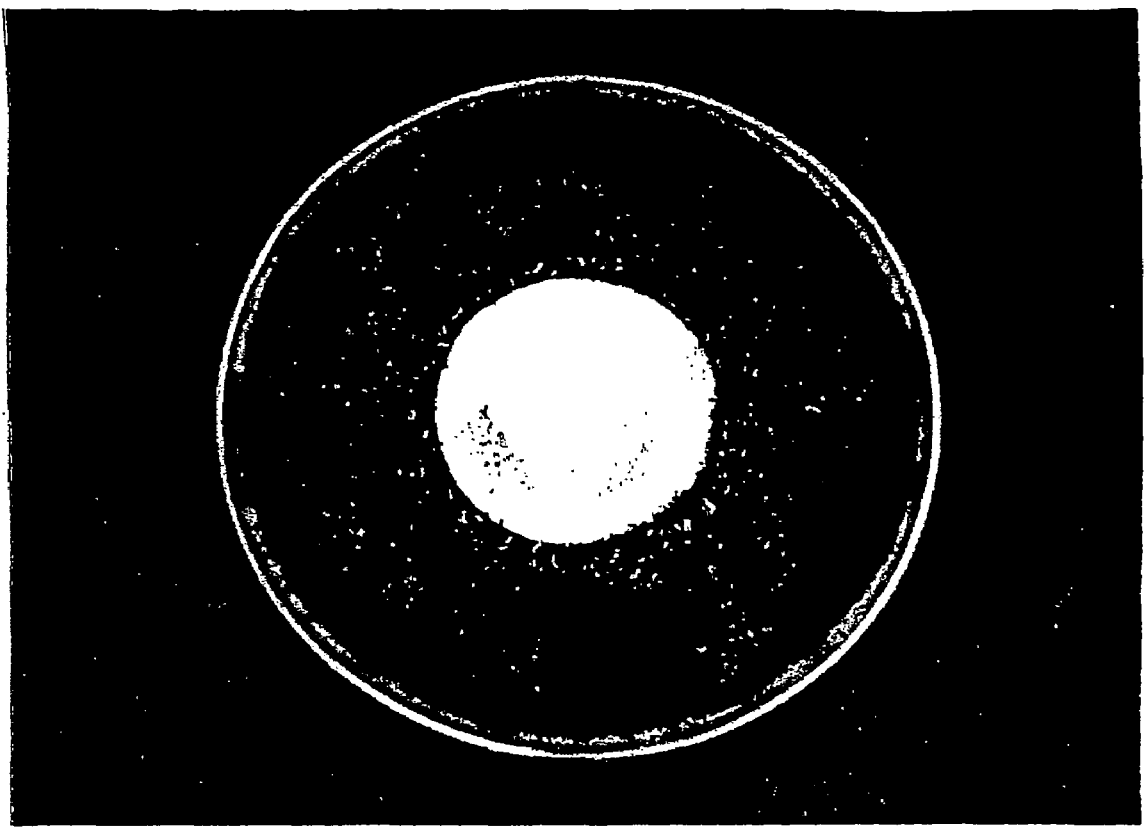
FIG. 9 is a picture of an acrylic disk after plating and incubation.

FIG. 9 shows an example of a plated acrylic sample after a period of incubation.

Figure 10:
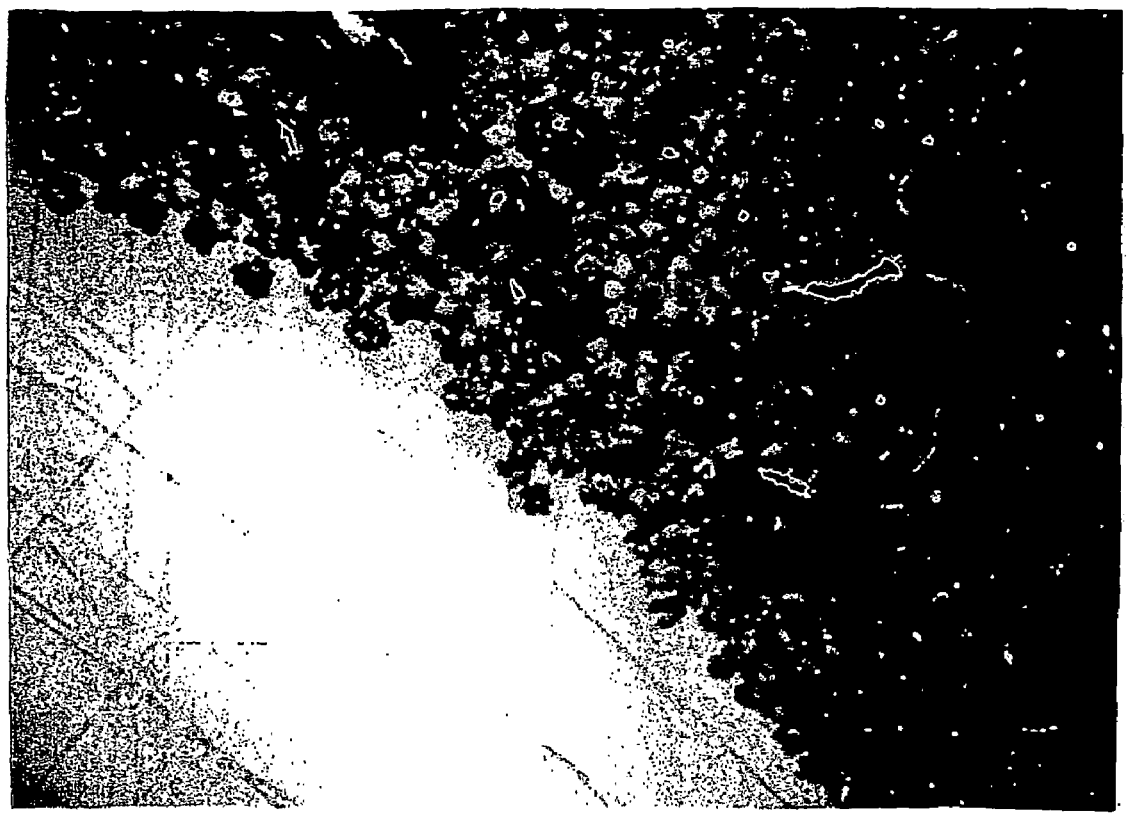
FIG. 10 is a picture of an acrylic disk that contains no antimicrobial agent after inoculation with a fungal species.

FIG. 10 is a picture taken along the edge of a section of a control disk which contained no antimicrobial agent. Significant fungal overlap is present along the edges of the disk.

Figure 11:
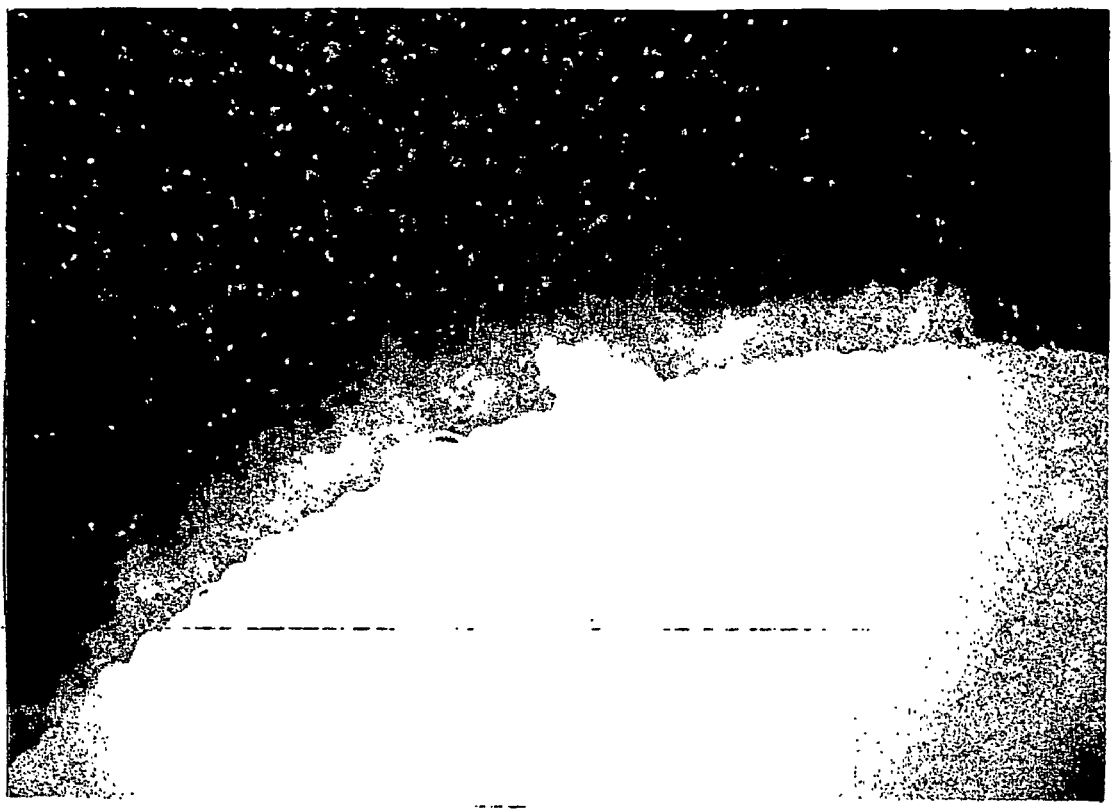
FIG. 11 is a picture taken along the edge of a disk made from the composition described in Table 7 of the Examples after inoculation with a fungal species.

FIG. 11 is a picture taken along the edge of a disk made from the composition described in Table 7. The edges of the disk showed excellent resistance to fungal coverage. The sample surface was extremely clean.

Figure 12:
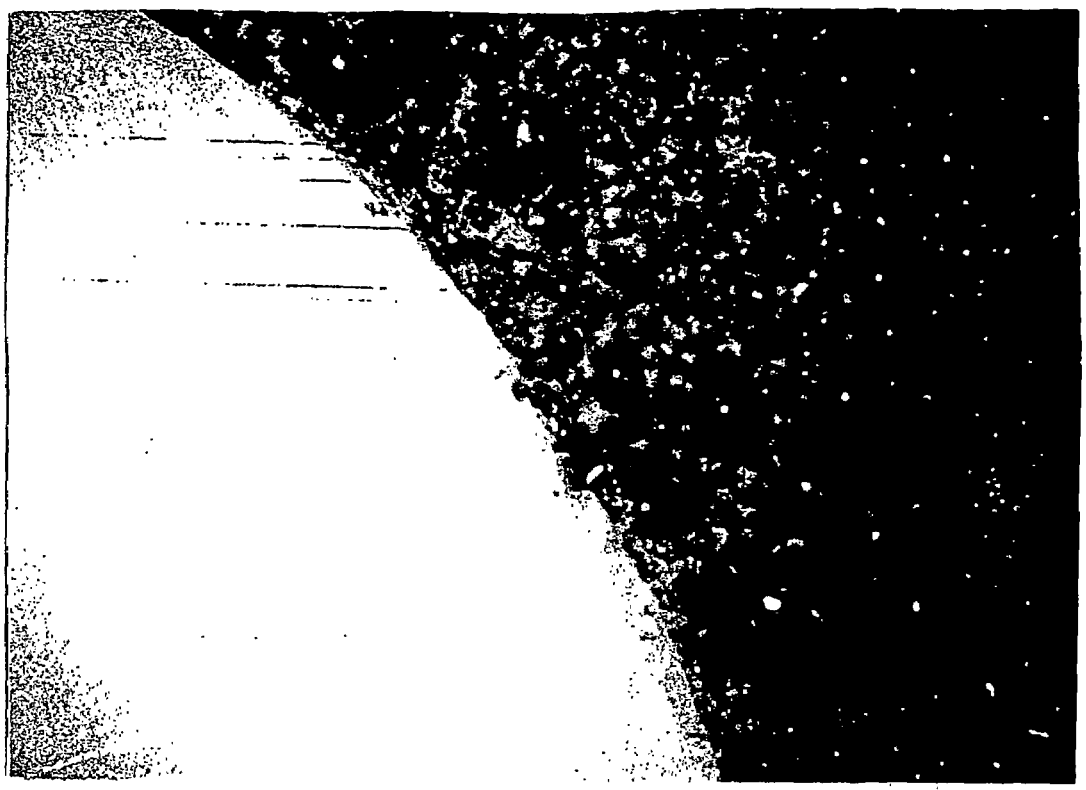
FIG. 12 is a picture taken along the edge of a disk made from the composition described in Table 8 of the Examples after inoculation with a fungal species.

FIG. 12 is a picture taken along the edge of a disk made from the composition described in Table 8. Resistance against fungal growth was minimal. There were microscopic signs of fungal overlap over the edge of the disk.

Figure 13:
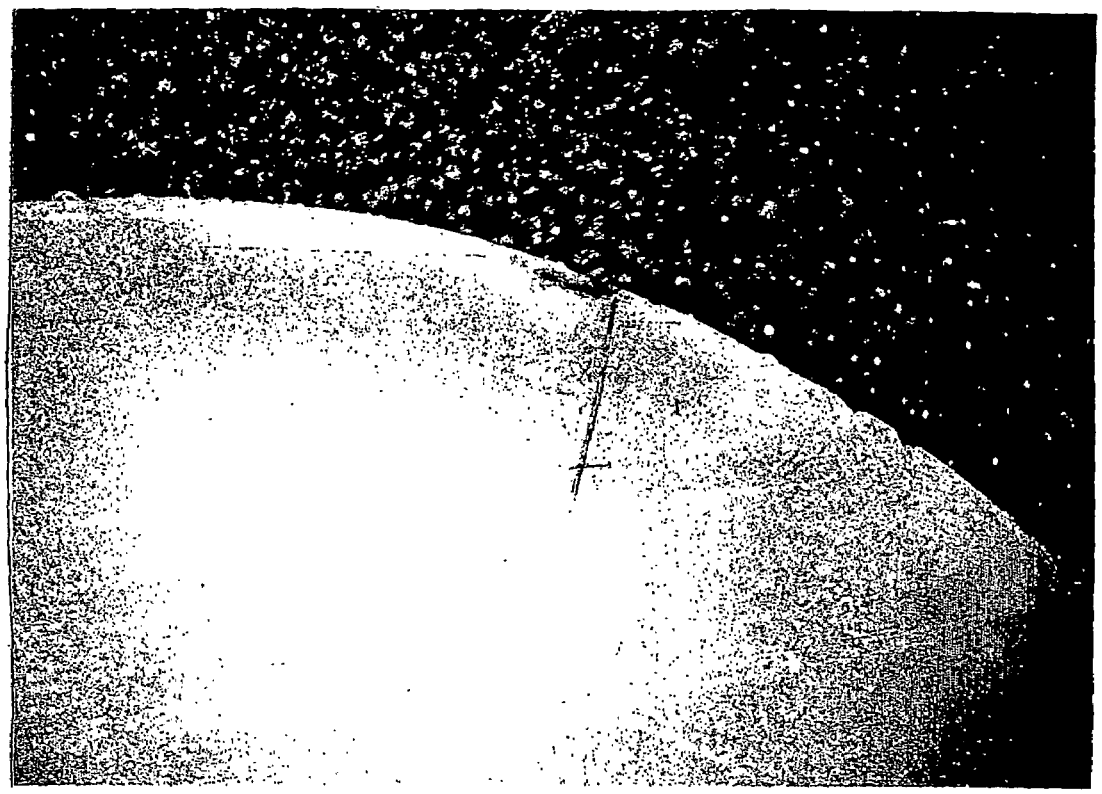
FIG. 13 is a picture taken along the edge of a disk made from the composition described in Table 9 of the Examples after inoculation with a fungal species.

FIG. 13 is a picture taken along the edge of a disk made from the composition described in Table 9. The disk was clean but there were the beginnings of fungal overlap onto the surface of the disk.

Figure 14:
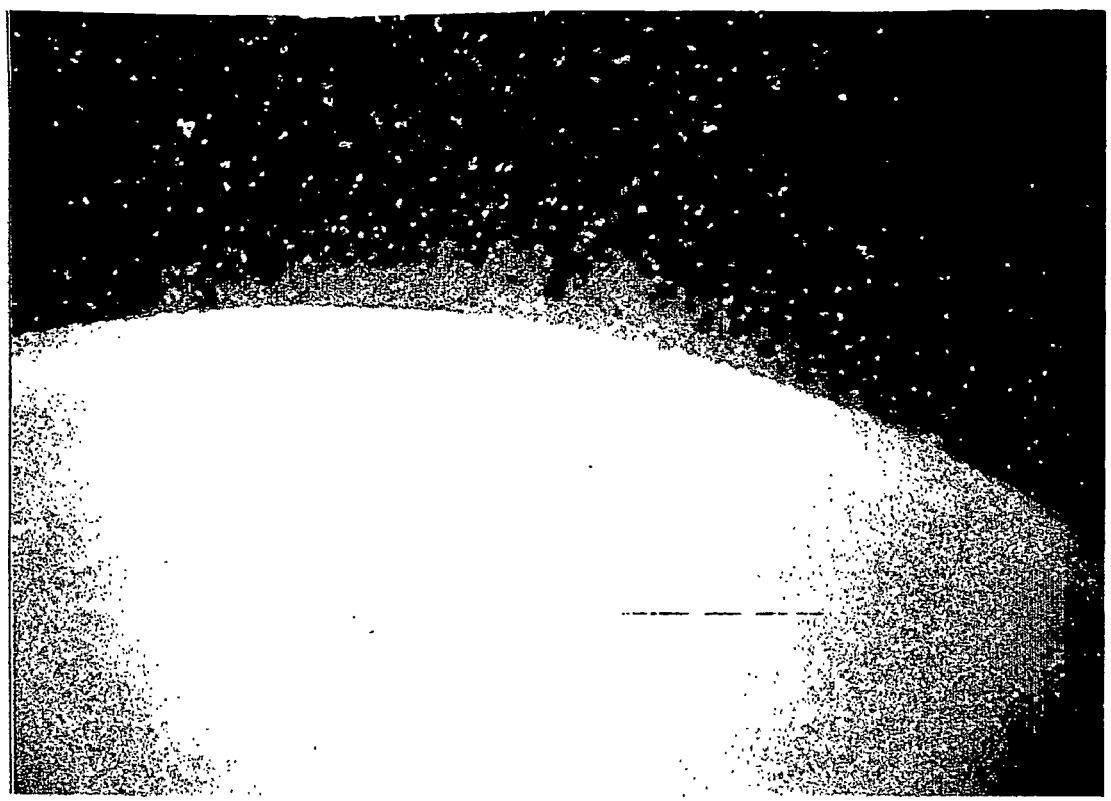
FIG. 14 is a picture taken along the edge of a disk made from the composition described in Table 10 of the Examples after inoculation with a fungal species.

FIG. 14 is a picture taken along the edge of a disk made from the composition described in Table 10. Excellent antifungal efficacy was demonstrated. There were microscopic signs of fungal overlap over the edge of the disk.

Figure 15:
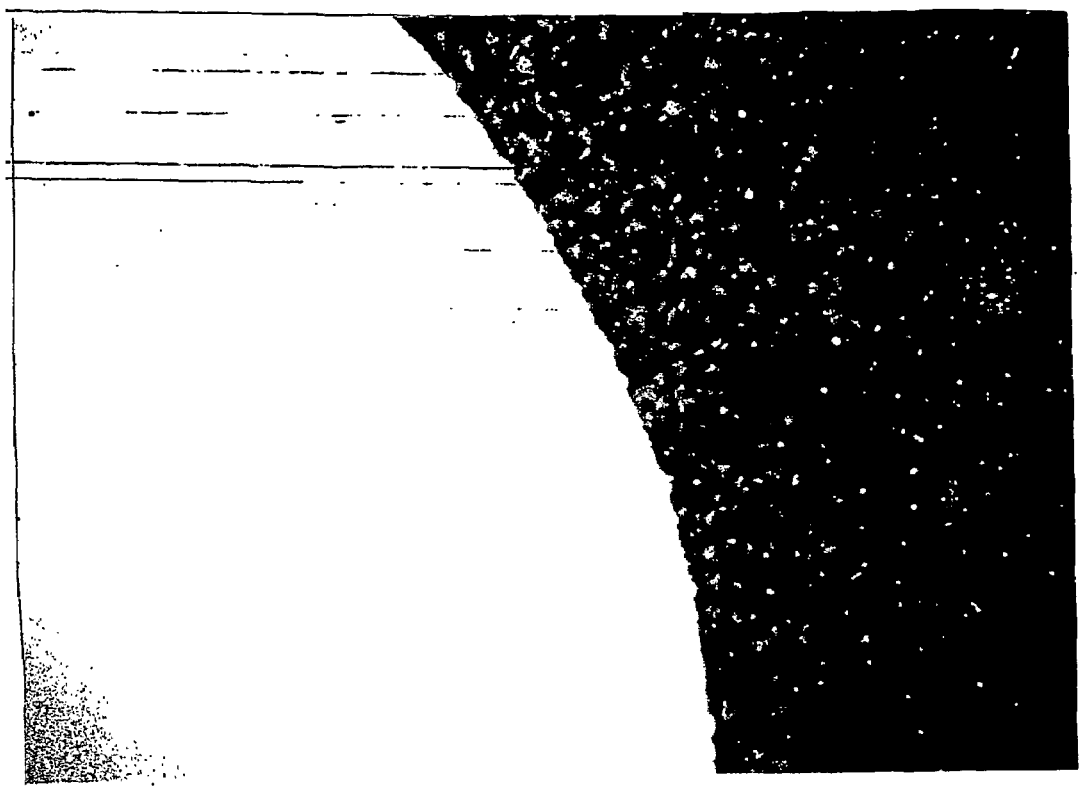
FIG. 15 is a picture taken along the edge of a disk made from the composition described in Table 11 of the Examples after inoculation with a fungal species.

FIG. 15 is a picture taken along the edge of a disk made from the composition described in Table 11. The disk showed very clean edges and surfaces.

Figure 16:
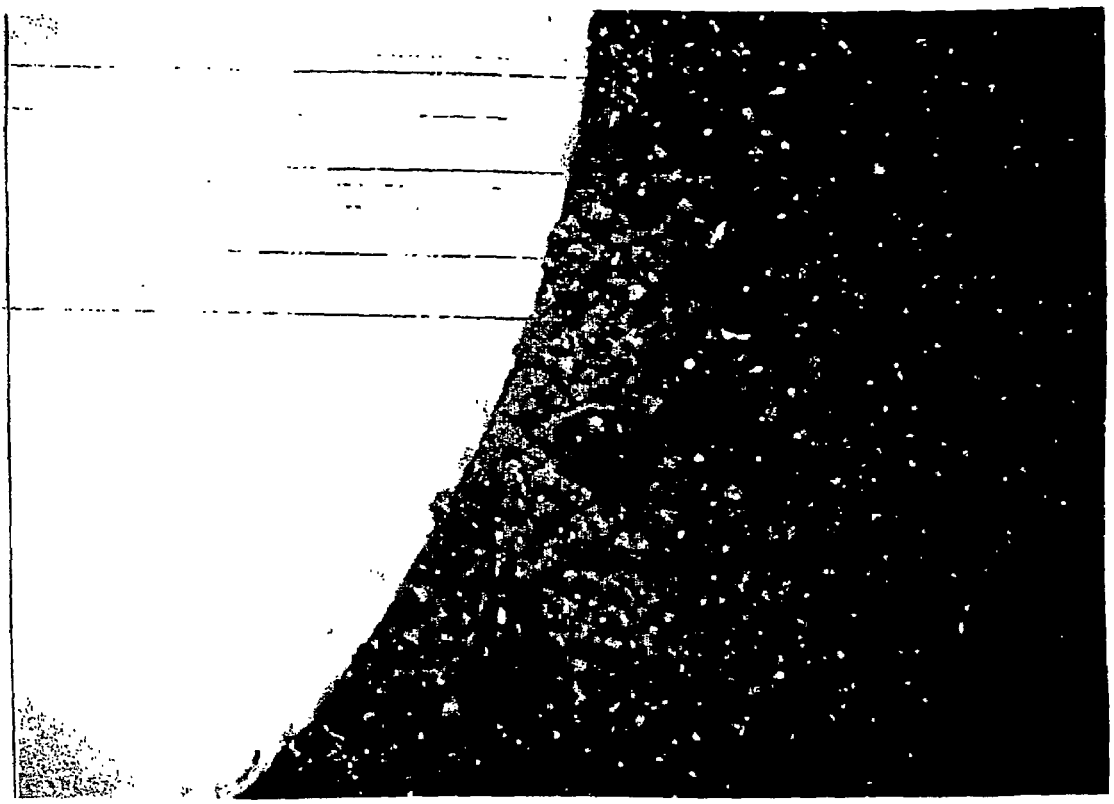
FIG. 16 is a picture taken along the edge of a disk made from the composition described in Table 12 of the Examples after inoculation with a fungal species.

FIG. 16 is a picture taken along the edge of a disk made from the composition described in Table 12. Resistance against fungal growth was minimal.

Figure 17:
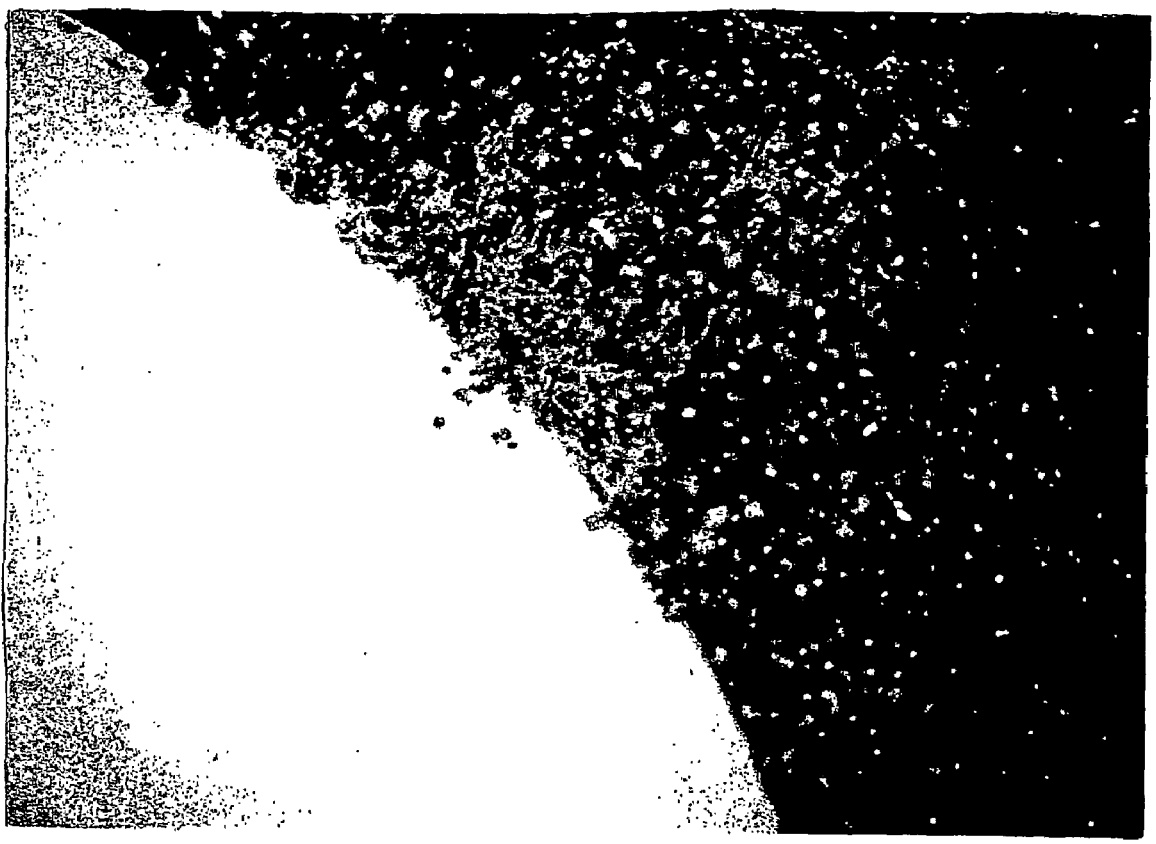
FIG. 17 is a picture taken along the edge of a disk made from the composition described in Table 13 of the Examples after inoculation with a fungal species.

FIG. 17 is a picture taken along the edge of a disk made from the composition described in Table 13. Resistance against fungal growth was minimal.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

That which is claimed is:

1. A method of manufacturing an antifungal acrylic polymer composition comprising:
   combining a quantity of an antifungal agent and an acrylic precursor solution; and
   polymerizing the precursor solution to form an acrylic polymer composition;
   wherein the weight concentration of antifungal agent in the polymer composition is in a range from about 250 ppm to about 50,000 ppm based upon the weight of the polymer composition; and
   wherein the antifungal agent is selected from the group consisting of isothiazoline, an oxathiazine, an azole, and a mixture thereof.

2. The method according to claim 1, wherein the antifungal agent is an isothiazoline selected from the group consisting of 2-n-octyl-4-isothiazolin-3-one and N-butyl-1,2 benzisothiazolin-3-one.

3. The method according to claim 1, wherein the oxathiazine is bethoxazin.

4. The method according to claim 1, wherein the antifungal agent is an azole selected from the group consisting of propiconazole, tebuconazole, and a mixture thereof.

5. The method according to claim 1, further comprising forming the antifungal acrylic polymer composition into a thermoformable sheet.

6. The method according to claim 1, wherein the antifungal agent is present in an amount from about 500 ppm to about 10,000 ppm.

7. The method according to claim 5, further comprising molding the thermoformable acrylic sheet into a product.

8. The method according to claim 7, wherein the product is selected from the group consisting of windshields, skylights, outdoor signs, boat surfaces, automobile tail lights, display cases, light fixtures, shower stalls, spas, bathroom basins, and counter tops, hot tubs, shelving, decorative laminates and other structural items.

\* \* \* \* \*